(12) United States Patent
Coufal

(10) Patent No.: US 6,410,727 B1
(45) Date of Patent: Jun. 25, 2002

(54) METHOD FOR PURIFYING MELAMINE

(75) Inventor: Gerhard Coufal, Leonding (AT)

(73) Assignee: Agrolinz Melamin GmbH, Linz (AT)

( * ) Notice: Subject to any disclaimer, the term of this patent is extended or adjusted under 35 U.S.C. 154(b) by 0 days.

(21) Appl. No.: 09/857,414

(22) PCT Filed: Dec. 16, 1999

(86) PCT No.: PCT/EP99/10008

§ 371 (c)(1),
(2), (4) Date: Jun. 4, 2001

(87) PCT Pub. No.: WO00/39107

PCT Pub. Date: Jul. 6, 2000

(30) Foreign Application Priority Data

Dec. 23, 1998 (AT) ............................................... 2166/98

(51) Int. Cl.⁷ ............................................ C07D 251/62
(52) U.S. Cl. ........................................ 544/203; 544/201
(58) Field of Search ................................... 544/201, 203

(56) References Cited

U.S. PATENT DOCUMENTS 4,465,832 A * 8/1984 De Wit et al. .............. 544/201
5,514,797 A   5/1996 Best et al. .................. 544/203
5,721,363 A   2/1998 Canzi et al. ................ 544/201

FOREIGN PATENT DOCUMENTS

| WO | 96/20182 | 7/1996 |
| WO | 96/20183 | 7/1996 |
| WO | 96/23778 | 8/1996 |
| WO | 97/20826 | 6/1997 |
| WO | 99/38852 | 8/1999 |

* cited by examiner

Primary Examiner—Mukund J. Shah
Assistant Examiner—Venkataraman Balasubramanian
(74) Attorney, Agent, or Firm—Wenderoth, Lind & Ponack, LLP

(57) ABSTRACT

The invention relates to a method for purifying melamine in which impure melamine is heated to a temperature range above 325°C. but lower than the melting point of melamine which depends on the prevailing ammonia pressure. In addition, the impure melamine is held in said temperature range under an ammonia pressure ranging from 1 to 150 bar for a duration lasting from 1 minute up to 20 hours. The melamine is provided in solid form. Afterwards, the melamine is relieved from pressure and cooled in any order.

8 Claims, No Drawings

METHOD FOR PURIFYING MELAMINE

The invention relates to a method for purifying melamine, in which solid melamine is allowed to dwell under ammonia pressure close to the melting point.

Melamine is preferably produced by pyrolysis of urea, it being possible to use both low-pressure processes and high-pressure processes, as described, for example, in "Ullmann's Encyclopedia of Industrial Chemistry, Vol. A 16, 5$^{th}$ ed (1990), pages 171–185". The crude melamine obtained in the melamine synthesis contains about 94–98% by weight of melamine, depending on the production process, and in particular melam, melem, melone, ureidomelamine, ammeline and ammelide as substantial impurities and must be further purified for more critical applications by additional process steps, such as, for example, recrystallization, or by a special procedure during the isolation, such as, for example, slow cooling, as described, for example, in WO96/20182, by a special temperature programme before the solidification, as described, for example, in WO96/23778, or by dwelling of the solid melamine under ammonia pressure, as described, for example, in WO96/20183, or by a combination of these process steps.

It was still the object, however, to find novel process variants which lead to a further increase in the melamine purity or to obtain purer melamine in a simpler manner, optionally also at pressures which are not so high.

It was unexpectedly found that more impurities are present or are formed during the dwelling of melamine under ammonia pressure both at temperatures well below the melting point and at temperatures just above the melting point than during the dwelling at temperatures in the solid range just below the melting point.

The invention accordingly relates to a method for purifying melamine, characterized in that impure melamine is brought into a temperature range $T_T$ above 325° C. but lower than the melting point of the melamine which depends on the respective prevailing ammonia pressure and is kept in this temperature range at an ammonia pressure of from 1 to 150 bar for the duration of from 1 minute to 20 hours, the melamine being present as a solid in this temperature range, after which, in any desired order, the pressure is relieved and, if desired, cooling to room temperature is effected and pure melamine is obtained in solid form. The dwelling, according to the invention, of the solid melamine (tempering) is preferably carried out in a temperature range $T_T$ between 330° C. (or particularly preferably between 335° C.) and the melting point of melamine which depends on the respective ammonia pressure.

The temperature can be kept constant during tempering but it can also be changed within the temperature range $T_T$ described above. Thus, the temperature can be decreased or increased, for example continuously or discontinuously, within the limits of the temperature range $T_T$.

According to the invention, the pressure during the tempering is preferably between 5 and 100 bar, particularly preferably between 10 and 50 bar. The dwell time during the tempering according to the invention is preferably from 6 min to 10 h, particularly preferably from 3 min to 5 h. The dwell time depends in particular on the desired purity of the melamine; the longer the duration of tempering, the purer is the melamine obtained. The dwell time is dependent on the respective process conditions. In order to obtain a specific purity, a shorter dwell time is accordingly sufficient in each case at higher temperatures and at higher pressures.

The purification method (tempering) according to the invention can be preferably carried out by a procedure in which either impure solid melamine is heated, or impure liquid melamine is cooled, to the temperature range (tempering range) $T_T$ and is allowed to dwell there.

After the end of the tempering, it is possible, depending on the technical conditions, first to cool and then to relieve the pressure or, conversely, first to relieve the pressure and then to cool. These steps can optionally be carried out in a further reaction apparatus. Melamine is preferably cooled to room temperature, for example with the aid of heat exchangers, by simple removal of the heating medium or by mixing with cold gases. By means of the method according to the invention, melamine is obtained in crystalline form or as a powder and has in particular a substantially reduced content of melam, melem and ammelide, which in some cases is even below the limit of detection.

The method according to the invention can be carried out both batchwise and continuously.

The melamine purification according to the invention is suitable in particular after a process for the production of melamine, in particular after any desired high-pressure process for the production of melamine from urea, in which the melamine is initially obtained in liquid form as a melt. It is advantageous to cool the ammonia-containing melamine melt prior to solidification, in particular by supplying further ammonia at about 1 to 50° C. above the pressure-dependent melting point of the melamine. The subsequent solidification is preferably effected in a fluidized bed by bringing into contact with cold solid inert substances or solid melamine. The method according to the invention can advantageously also be carried out after any other desired working-up steps of high-pressure processes. These working-up steps include in particular:

a) separation of the $NH_3/CO_2$ gas mixture (off-gases) obtained in the melamine synthesis of the liquid melamine,
b) reduction of the $CO_2$ dissolved in the melamine by introduction of $NH_3$ (stripping),
c) allowing the liquid melamine to dwell in the presence of ammonia (ageing),
d) cooling and solidification of the melamine, for example with water, with aqueous melamine-containing solutions or suspensions, with cold gases, such as gaseous ammonia, with liquid ammonia or with cold solid inert substances or solid melamine according to WO99/38852, for example in a fluidized bed. The melamine melt can, for example according to WO97/20826, be sprayed into a cooling container in which an ammonia atmosphere is present.

The purification method according to the invention is carried out after the solidification step, and the number of other preceding working-up steps carried out can be varied according to the respective circumstances. The working-up of the melamine obtained from urea by a high-pressure process, up to the solidification step, may thus comprise any desired combination or only one of these steps.

According to the invention, the purification of melamine of any purity is possible. The purity of a crude melamine from a melamine production process is, for example, 94–98% by weight, depending on the melamine process used, the melamine being contaminated in particular with melam, melem and ammelide. It is however also possible according to the invention further to purify more highly impure melamines as well as melamines of higher purity which have already been purified by other purification methods. It is possible to obtain melamine having a purity of up to more than 99.9% by weight, in some cases more than 99.99% by weight, depending on the pressure, temperature, dwell time and initial purity used.

EXAMPLES

The starting material used in each case was a melamine which originated from a high-pressure pilot plant for the production of melamine from urea and had a purity of 98.6% by weight and was contaminated in particular with 1.3% by weight of melam and about 0.1% by weight of further byproducts, such as, for example, melem or ammelide (corresponding to Example A in Table 1). The analytical determination of melam, melem and ammelide was carried out by means of HPLC.

Examples 1 to 5

Melamine and the amount of ammonia required for achieving the desired pressure were introduced into a laboratory autoclave. Thereafter, the autoclave was heated to a temperature of 340° C. or 330° C. and left to dwell at the respective pressure for 60 min. The autoclave was then rapidly cooled to 280° C. with water, the pressure was relieved and the melamine was analyzed by means of HPLC. The respective pressures and temperatures during the tempering and the content of byproducts (melam, melem, ammelide) in the starting melamine (Example A) and in the melamine after the tempering (Examples 1–5) are listed in Table 1.

TABLE 1

| | | Melamine after tempering for 60 min | | |
|---------|------------------|----------------|----------------|--------------------|
| Example | Pressure (bar) | Temp. (° C.) | Melam (ppm) | Melem (ppm) | Ammelide (ppm) |
| A* | — | — | 12630 | 431 | 155 |
| 1 | 10 | 340 | 323 | 177 | — |
| 2 | 20 | 340 | 443 | 319 | — |
| 3 | 40 | 340 | 131 | 252 | 39 |
| 4 | 70 | 340 | 58 | 122 | — |
| 5 | 100 | 330 | 105 | 162 | — |

Limit of detection 2 ppm
*Starting melamine

What is claimed is:

1. Method for purifying melamine, characterized in that impure melamine is brought into a temperature range $T_T$ above 325° C. and lower than the melting point of melamine which depends on the respective prevailing ammonia pressure and is kept in this temperature range at an ammonia pressure of from 1 to 150 bar for the duration of from 1 minute to 20 hours, the melamine being present in this temperature range as a solid, after which, in any desired order, the pressure is relieved, cooling is effected and pure melamine is obtained in solid form.

2. Method according to claim 1, characterized in that impure liquid melamine is brought into the temperature range $T_T$.

3. Method according to claim 1, characterized in that impure solid melamine is brought into the temperature range $T_T$.

4. Method according to claim 1, characterized in that the impure melamine is brought into a temperature range which is between 330° C. and the melting point of melamine which depends on the respective prevailing ammonia pressure.

5. Method according to claim 1, characterized in that the ammonia pressure is between 5 and 100 bar.

6. Method according to claim 1, characterized in that the melamine is kept in the temperature range $T_T$ for a duration of from 5 minutes to 10 hours.

7. Method according to claim 1, characterized in that the method is carried out after a process for the production of melamine.

8. Method according to claim 1, characterized in that the method is carried out after a high-pressure process for the production of melamine from urea, in which liquid melamine, optionally after being allowed to dwell in the presence of ammonia (ageing) is solidified in a fluidized bed by being brought into contact with cold solid inert substances or solid melamine and is then kept in a temperature range $T_T$ above 325° C. and lower than the melting point of melamine which depends on the effective prevailing ammonia pressure, at an ammonia pressure of from 1 to 150 bar for the duration of from 1 minute to 20 hours, after which, in any desired order, the pressure is relieved, cooling is effected and pure melamine is obtained in solid form.

* * * * *